United States Patent
Tesson et al.

(10) Patent No.: US 11,214,547 B2
(45) Date of Patent: Jan. 4, 2022

(54) CRYSTALLINE ELTROMBOPAG MONOETHANOLAMINE SALT FORM D

(71) Applicant: F.I.S.—FABBRICA ITALIANA SINTETICI S.P.A., Montecchio Maggiore (IT)

(72) Inventors: Nicolas Tesson, Esplugues de Llobregat Barcelona (ES); Jordi De Mier Vinue, Esplugues de Llobregat Barcelona (ES); Paolo Stabile, Montecchio Maggiore (IT); Pierluigi Padovan, Montecchio Maggiore (IT); Matteo De Poli, Montecchio Maggiore (IT); Angelo Restelli, Montecchio Maggiore (IT)

(73) Assignee: F.I.S.—FABBRICA ITALIANA SINTETICI S.P.A., Montecchio Maggiore (IT)

( * ) Notice: Subject to any disclaimer, the term of this patent is extended or adjusted under 35 U.S.C. 154(b) by 0 days.

(21) Appl. No.: 17/263,636

(22) PCT Filed: Jul. 25, 2019

(86) PCT No.: PCT/EP2019/070050
§ 371 (c)(1),
(2) Date: Jan. 27, 2021

(87) PCT Pub. No.: WO2020/025444
PCT Pub. Date: Feb. 6, 2020

(65) Prior Publication Data
US 2021/0198211 A1    Jul. 1, 2021

(30) Foreign Application Priority Data
Aug. 2, 2018 (EP) .................................... 18187070

(51) Int. Cl.
*C07D 231/46* (2006.01)

(52) U.S. Cl.
CPC ........ *C07D 231/46* (2013.01); *C07B 2200/13* (2013.01)

(58) Field of Classification Search
CPC .................................................... C07D 231/46
See application file for complete search history.

(56) References Cited

U.S. PATENT DOCUMENTS

| 8,372,822 | B2 | 2/2013 | Leksic et al. |
| 2010/0256212 | A1 | 10/2010 | Leksic et al. |
| 2015/0087845 | A1* | 3/2015 | Upadhye .............. C07D 231/46 548/367.4 |

FOREIGN PATENT DOCUMENTS

| WO | 0189457 A2 | 11/2001 |
| WO | 03098992 A2 | 12/2003 |
| WO | 2010114943 A1 | 10/2010 |

OTHER PUBLICATIONS

International Search Report and Written Opinion for Corresponding International Application No. PCT/EP2019/070050 (13 Pages) (dated Oct. 25, 2019).

* cited by examiner

*Primary Examiner* — Shawquia Jackson
(74) *Attorney, Agent, or Firm* — Lucas & Mercanti, LLP

(57) ABSTRACT

Object of the present invention is a better crystalline form of Eltrombopag (ETP) monoethanolamine salt, named Form D, stable, suitable for pharmaceutical purposes, and with the highest solubility in water and excellent non-hygroscopicity, then the related process and intermediates thereof.

15 Claims, 8 Drawing Sheets

CRYSTALLINE ELTROMBOPAG MONOETHANOLAMINE SALT FORM D

CROSS-REFERENCE TO RELATED APPLICATIONS

This application is a 371 of PCT/EP2019/070050, filed Jul. 25, 2019, which claims the benefit of European Patent Application No. 18187070.0, filed Aug. 2, 2018.

TECHNICAL FIELD

The present invention refers to a crystalline Eltrombopag monoethanolamine salt form D, which is a solid form particularly stable and well suitable for pharmaceutical purposes.

BACKGROUND ART

Eltrombopag (abbreviate with the acronym ETP) is a small molecule, non-peptide thrombopoitin (TPO) receptor agonist that stimulates the proliferation and differentiation of megakaryocytes.

ETP has the following chemical formula (II):

(II)

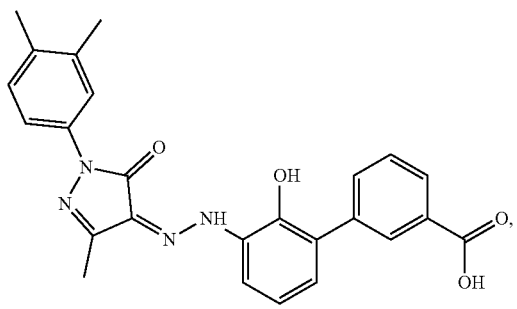

and has chemical name 3'-{(2Z)-2-[1-(3,4-dimethylphenyl)-3-methyl-5-oxo-1,5-dihydro-4H-pyrazol-4-ylidene]hydrazino}-2'-hydroxy-3-biphenyl carboxylic acid or 3'-{N'-[1-(3,4-dimethylphenyl)-3-methyl-5-oxo-1,5-dihydropyrazol-4-ylidene]hydrazino}-2'-hydroxybiphenyl-3-carboxylic acid.

This molecule is an active pharmaceutical ingredient, which is known in the market with the commercial name Promacta® in the USA and Revolade® in most countries outside the USA.

Specifically, ETP is used to treat adults and children one year of age and older with low blood platelet counts due to chronic immune (idiopathic) thrombocytopenia (ITP), when other medicines to treat ITP or surgery to remove the spleen have not worked well enough.

Eltrombopag is commercialized in pharmaceutical compositions comprising this active pharmaceutical ingredient in form of Eltrombopag olamine or ETP olamine, i.e. a salt of ETP with ethanolamine in 1:2 ratio, also called Eltrombopag bisethanolamine salt of formula (III):

(III)

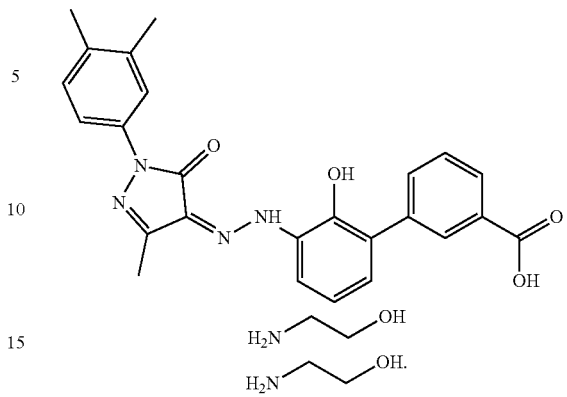

Eltrombopag olamine is supplied for oral administration in two strengths: 25 mg and 50 mg film-coated tablets.

This salt is a red/brown crystalline solid, sparingly soluble in water and non-hygroscopic. The molecule does not contain asymmetric centres although it exists as the Z-isomer in solution and the solid state. It is thermally stable up to about 125° C. At higher temperature, an endothermic reaction associated with its degradation occurs, as reported in Australian and European Public Assessment Reports.

A crystalline form of the above mentioned disalt is described by the originator in WO 03/098992, and other polymorphs of ETP olamine (example Form I, II, III, V and XVI) are disclosed in WO 2010/114943.

Moreover, an alternative to commercial ETP bisethanolamine salt is ETP monoethanolamine salt, which is used to prepare pharmaceutical formulation according to WO 2010/114943.

In particular, two crystalline Eltrombopag (ETP) monoethanolamine salt forms, i.e. ETP monoethanolamine salt Form H and ETP monoethanolamine salt Form E are described in WO 2010/114943.

Specifically, the paragraphs [00174] and [00175] of WO 2010/114943 disclose the XPRD peaks of ETP monoethanolamine salt form H, having characteristic peaks 2-Theta values (2θ) at: 4.9, 6.9, 15.1 and 23.0° 2θ±0.2°, and the process for preparing said Form H by crystallization of ETP bisethanolamine salt in 1-butanol or 1-pentanol, as shown in the examples 37 and 38.

Moreover, said WO 2010/114943 describes ETP monoethanolamine salt form E, at paragraphs [00176] and [00177], with its XPRD characteristic peaks 2-Theta values (2θ) at: 10.5, 13.4, 19.5 and 21.7° 2θ±0.2°, and the process for preparing it in 2,2,2-trifluoroethanol, shown in the example 39.

Both processes for the preparation of the above two different ETP monoethanolamine salt forms, i.e. Form H and Form E, are carried out starting from ETP bisethanolamine salt.

SUMMARY OF INVENTION

The problem addressed by the present invention is therefore that of providing a better crystalline form of Eltrombopag (ETP) monoethanolamine salt, process and intermediates thereof, which allows to get a better product compared to those of the prior art.

This problem is solved by the crystalline Eltrombopag (ETP) monoethanolamine salt form D, having the best non-hygroscopic behaviour compared to known ETP monoethanolamine salt Form H, the highest solubility in water and good thermodynamic stability therefore well suitable for pharmaceutical purposes.

The crystalline Eltrombopag (ETP) monoethanolamine salt form D is prepared by a process which passes through intermediates such as Eltrombopag ammonium salt, as outlined in the annexed claims, whose definitions are integral part of the present description.

Further features and advantages of the process according to the invention will result from the description hereafter reported of examples of realization of the invention, provided as an indication and not as a limitation of the invention.

DRAWINGS

DESCRIPTION OF EMBODIMENTS

Figure 1:
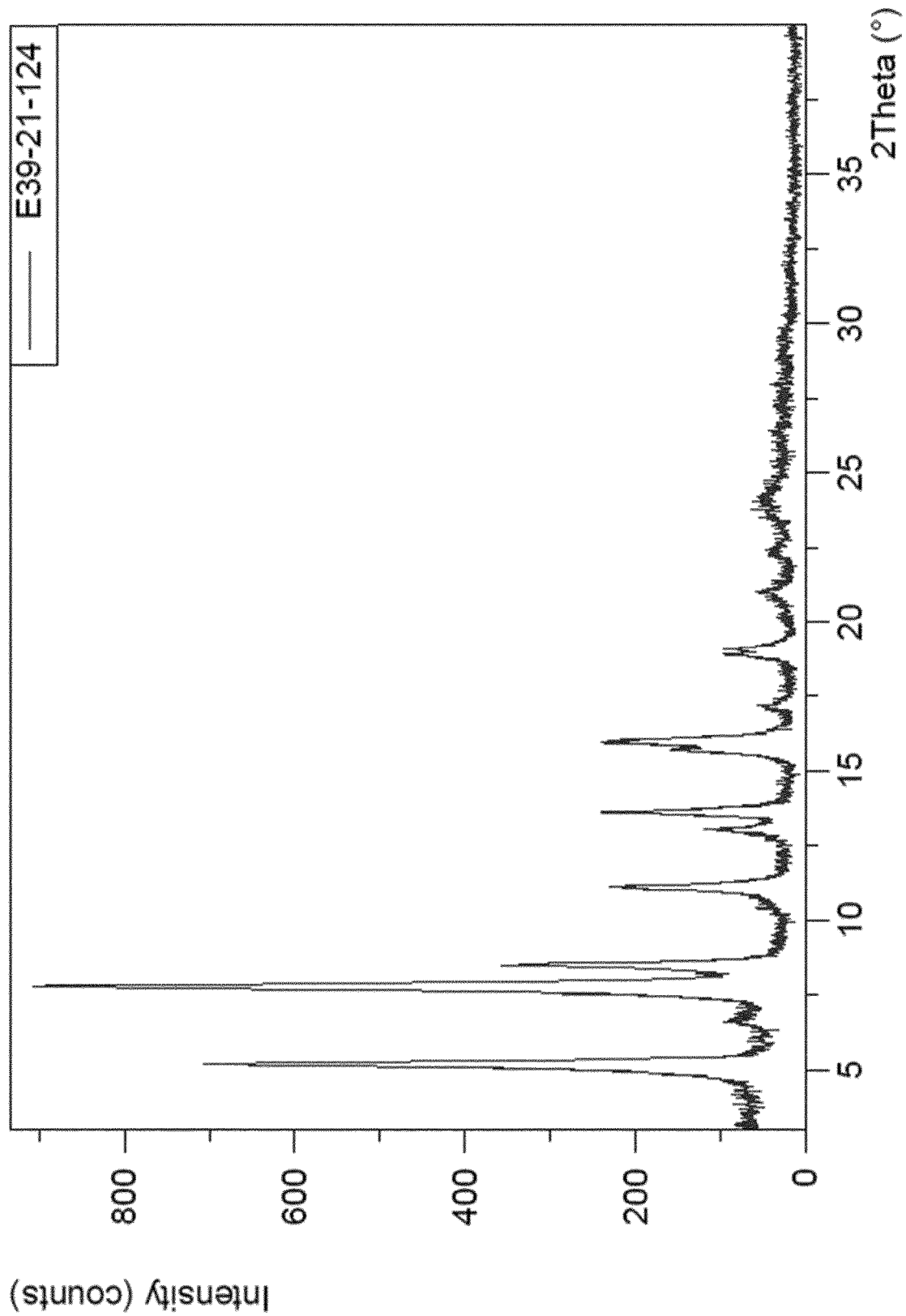
FIG. 1 shows the powder x-ray diffraction pattern of Eltrombopag monoethanolamine salt form D of formula (I), obtained by the step c) of the process of the present invention.

Object of the present invention is a crystalline Eltrombopag monoethanolamine salt Form D of formula (I):

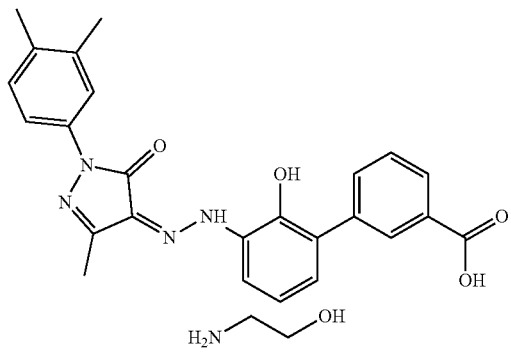

(I)

having one of the following characteristic peaks of X-ray powder diffraction pattern expressed in 2-Theta values (2θ) at: 7.8, 11.1 and 19.1, each peak±0.2.

It has been indeed surprisingly found that the crystalline form of Eltrombopag monoethanolamine salt Form D is stable and well suitable to be employed for pharmaceutical purposes. Moreover, it has been surprising that the above mentioned crystalline form can be produced by means of a salification of a suspension of Eltrombopag with ammonia to give Eltrombopag ammonium salt, according to the present invention, in particular to produce one or two crystalline Eltrombopag ammonium salt forms or mixture thereof. The latest forms, i.e. ETP ammonium salt Form C1 and ETP ammonium salt Form C2, provide a crystalline Eltrombopag monoethanolamine salt Form D.

In particular, the salification process produces one or two crystalline Eltrombopag ammonium salt forms or mixture thereof, which are defined and characterized as ETP ammonium salt Form C1 and ETP ammonium salt Form C2.

Indeed, the present invention provides a different process to provide a crystalline Eltrombopag monoethanolamine salt, compared to the above mentioned prior art, wherein ETP monoethanolamine salt (solid form H and E) are produced starting from ETP bisethanolamine salt.

Furthermore, it has been observed that said ETP monoethanolamine salt Form D has a value of DSC onset, measured by DSC analysis, higher than other ETP monoethanolamine salt forms. This is evidence of the thermodynamic stability of the product.

Another very important advantage of the product of the present invention is that said ETP monoethanolamine salt Form D is stable, under ICH guidelines accelerated stability conditions, as better described later and in the experimental part. This better stability is important in the pharmaceutical composition, since it guarantees efficacy and safety of the pharmaceutical product.

Finally, ETP monoethanolamine salt Form D, being stable under stability ICH guideline conditions, can be a good alternative to other known ETP monoethanolamine salt forms (i.e. ETP monoethanolamine salt Form H and ETP monoethanolamine salt Form E) for the preparation of pharmaceutical composition.

The crystalline Eltrombopag (ETP) monoethanolamine salt Form D of formula (I) of the present invention has one of the following characteristic peaks of X-ray powder diffraction pattern expressed in 2-Theta values (2θ) at: 7.8, 11.1 and 19.1, each peak±0.2.

According to a preferred embodiment of the product of the present invention, said crystalline ETP monoethanolamine salt Form D of formula (I) of the present invention has one of the following characteristic peaks of X-ray powder diffraction pattern expressed in 2-Theta values (2θ) at: 7.8, 11.1 and 19.1, each peak±0.1.

According to a preferred embodiment of the present invention, the crystalline ETP monoethanolamine salt Form D of formula (I) has two or three of the following characteristic peaks of X-ray powder diffraction pattern expressed in 2-Theta values (2θ) at: 7.8, 11.1 and 19.1, each peak±0.2; preferably each peak±0.1.

According to more preferred embodiment of the present invention, the crystalline ETP monoethanolamine salt Form D of formula (I) has characteristic peaks of X-ray powder diffraction pattern expressed in 2-Theta values (2θ) at: 7.8, 8.6, 11.1, 18.9 and 19.1, each peak±0.2; preferably each peak±0.1.

According to a further preferred embodiment of the present invention, the crystalline ETP monoethanolamine salt Form D of formula (I) has characteristic peaks of X-ray powder diffraction pattern expressed in 2-Theta values (2θ) at: 7.8, 8.6, 11.1, 13.1, 16.0, 18.9 and 19.1, each peak±0.2; preferably each peak±0.1.

Moreover, the list of the values of the peaks of X-powder diffraction ray pattern expressed in 2-Theta values (2θ) of the crystalline ETP monoethanolamine salt Form D of formula (I) is following reported in Table 1, and shown in FIG. 1.

TABLE 1

| Pos. [° 2θ] | d-spacing [Å] | Rel. Int. [%] |
|---|---|---|
| 5.2 | 16.9 | 95 |
| 7.8 | 11.3 | 100 |
| 8.6 | 10.3 | 31 |
| 11.1 | 8.0 | 26 |
| 13.1 | 6.8 | 9 |
| 13.7 | 6.5 | 20 |
| 15.7 | 5.6 | 13 |
| 16.0 | 5.6 | 22 |
| 17.2 | 5.2 | 3 |
| 18.9 | 4.7 | 6 |
| 19.1 | 4.6 | 6 |
| 21.0 | 4.2 | 3 |
| 22.3 | 4.0 | 3 |
| 24.1 | 3.7 | 5 |

According to another preferred embodiment of the present invention, the crystalline Eltrombopag monoethanolamine salt Form D of formula (I) has DSC onset comprised in the range from 231° C. to 233° C. and/or DSC peak in the range 237° C. to 239° C.

Specifically, the value of the DSC onset and DSC peak is recorded as measured by DSC.

The DSC onset corresponds to the melting point recorded by DSC analysis, whose method is better described in the experimental part.

According to preferred embodiment of the present invention, the crystalline Eltrombopag monoethanolamine salt Form D has onset at about 232° C. as measured by DSC.

According to preferred embodiment of the present invention, the crystalline Eltrombopag monoethanolamine salt Form D has peak at about 238° C. as measured by DSC.

According to more preferred embodiment of the present invention, Eltrombopag monoethanolamine salt Form D has onset at about 232° C. and peak at about 238° C. both as measured by DSC.

Figure 2:
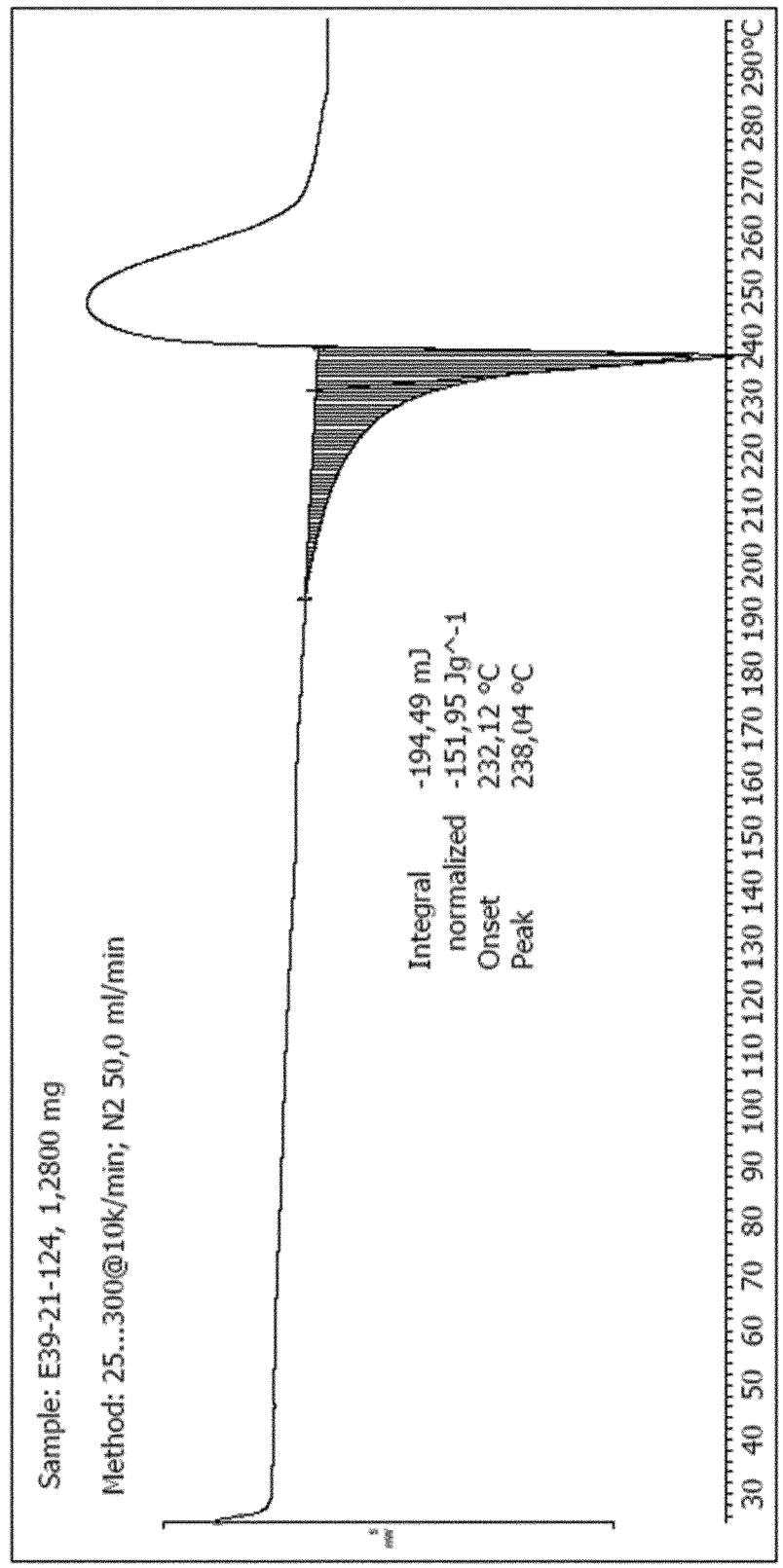
FIG. 2 shows the DSC curve of Eltrombopag monoethanolamine salt form D of formula (I), obtained by the step c) of the process of the present invention.

Specifically, DSC analysis shows one endothermic event with an onset at 232° C. and a peak at 238° C., the value of onset corresponds to the melting point of ETP monoethanolamine salt Form D, followed by large event due to a degradation event (see FIG. 2).

Figure 6:
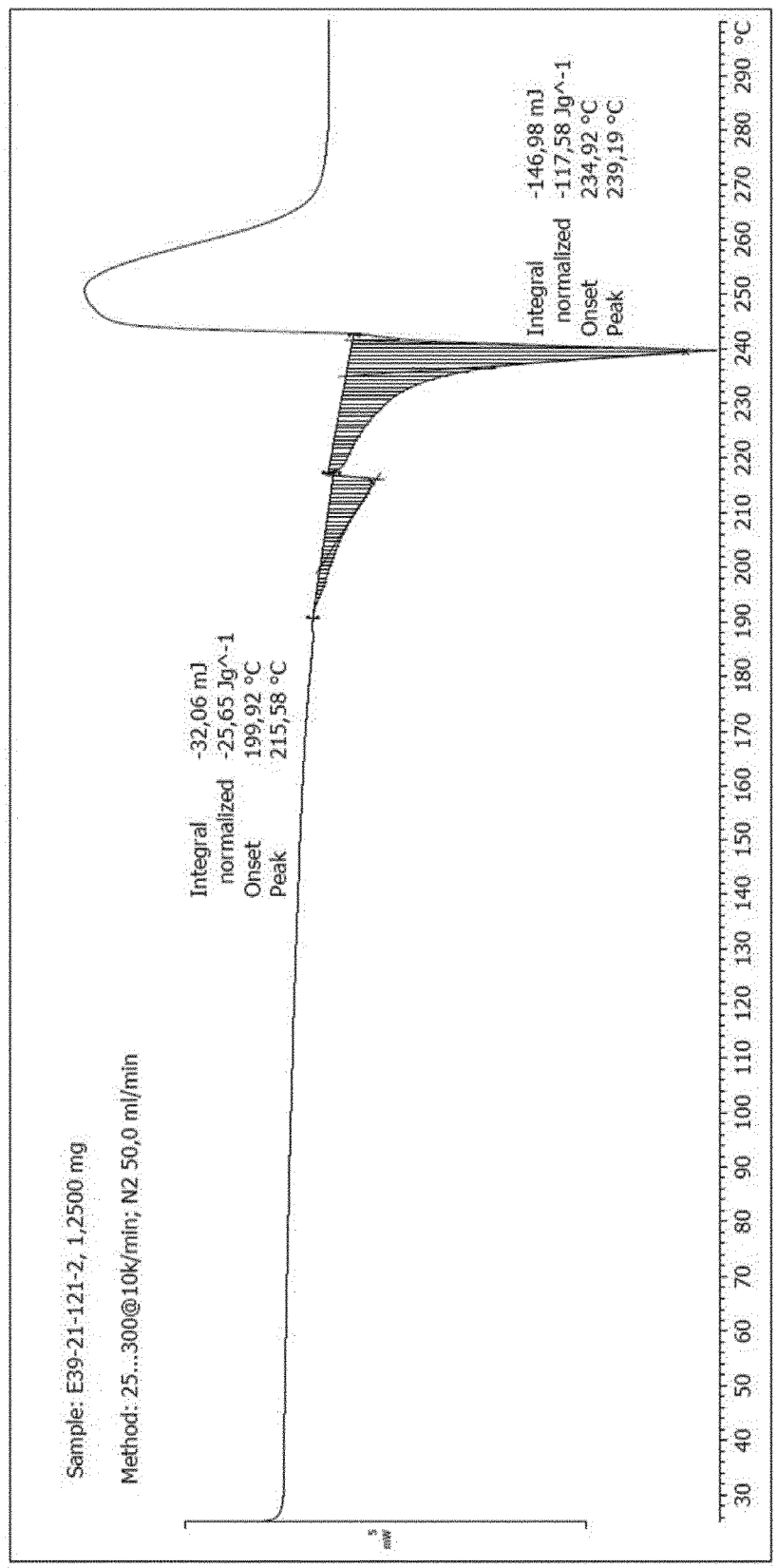
FIG. 6 shows the DSC curve of Eltrombopag monoethanolamine salt Form H.

Moreover, the above mentioned DSC analysis of the crystalline ETP monoethanolamine salt Form D shows a linear curve having only one onset and one peak, that is an evidence of the own better stability compared with DSC analysis of Eltrombopag monoethanolamine salt Form H, wherein there are two peaks, as shown in FIG. 6.

In particular, the DSC analysis of the crystalline ETP monoethanolamine salt Form H shows onset at about 199° C., i.e. melting point as measured by DSC, and peak at 215° C., moreover the same DSC analysis shows a second curve having an onset at about 234.9° C. and peak at 239.2° C.

Figure 7:
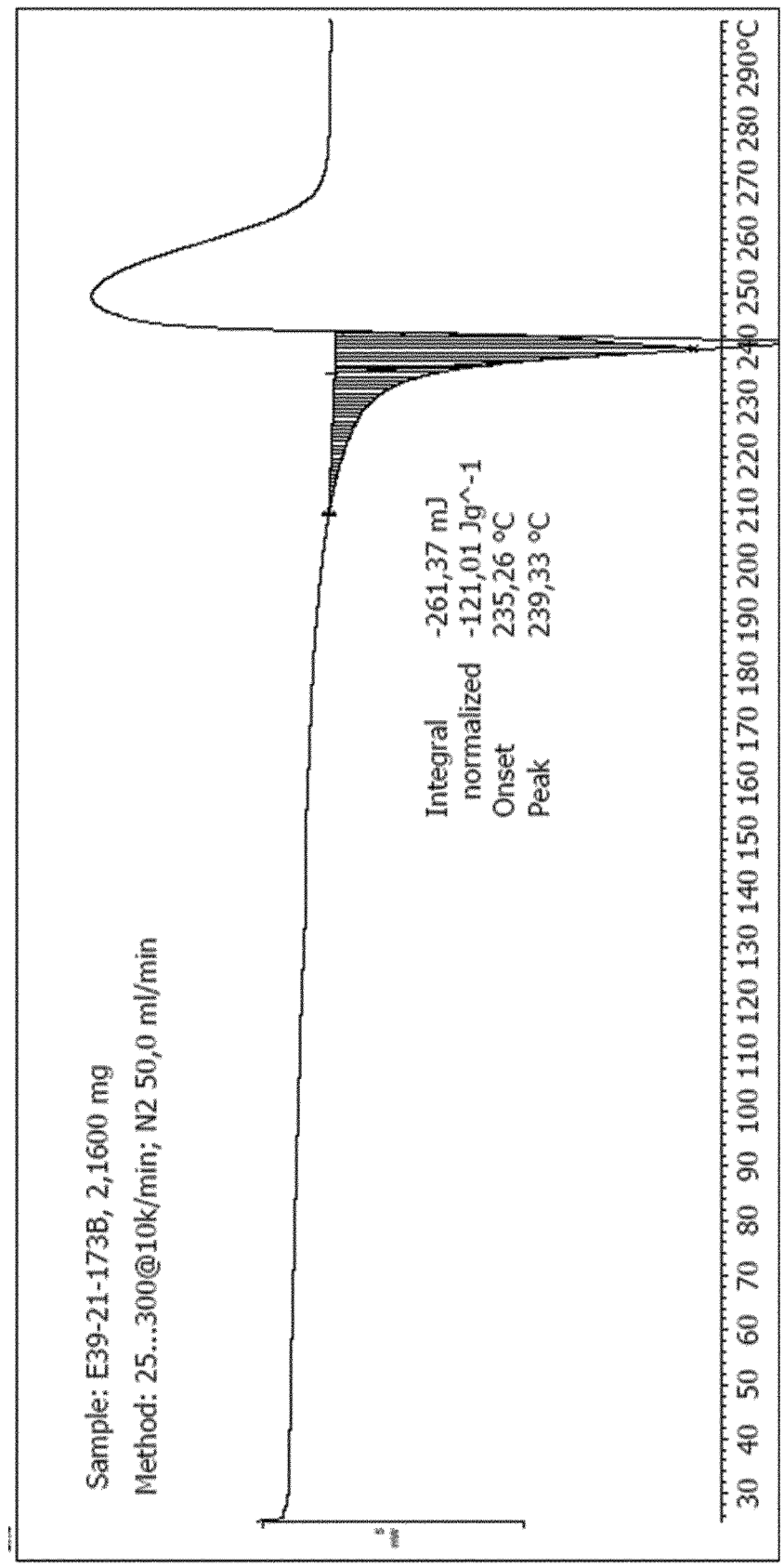
FIG. 7 shows the DSC curve of Eltrombopag monoethanolamine salt Form D1, further form of ETP monoethanolamine salt.

The second curve of said DSC analysis is exactly the same curve of the DSC analysis of crystalline Eltrombopag monoethanolamine salt Form D1, as shown in FIG. 7.

Said ETP monoethanolamine salt Form D1 was prepared following a process wherein the starting material is ETP free acid was heated at reflux in 1-butanol. After that, the resulting mixture is added ethanolamine, and all was stirred. The suspension was cooled down, filtered and dried to obtain ETP monoethanolamine salt Form D1.

ETP monoethanolamine salt Form D1 has a characteristic peak of X-ray powder diffraction pattern expressed in 2-Theta values (2θ) at 11.6±0.2.

The DSC analysis of ETP monoethanolamine salt Form D1 shows onset at about 234.9° C. and peak at 239.2° C., which is the same of that present in DSC analysis of ETP monoethanolamine salt Form H.

Therefore, ETP monoethanolamine salt Form H converts to ETP monoethanolamine salt Form D1 during the first thermal melting.

In order to confirm that above described, the characteristic peaks of X-ray powder diffraction pattern expressed in 2-Theta values (2θ) of ETP monoethanolamine salt Form H are at: 4.9, 6.9, 15.1 and 23.0°2θ±0.2°, and that of ETP monoethanolamine salt Form D1 is at: 11.6±0.2. The latest corresponds to the same product described in the DSC analysis having the second curve, i.e. ETP monoethanolamine salt Form D1.

Another aspect of the present invention is thus, the process for the preparation of the crystalline Eltrombopag monoethanolamine salt Form D of formula (I), above described:

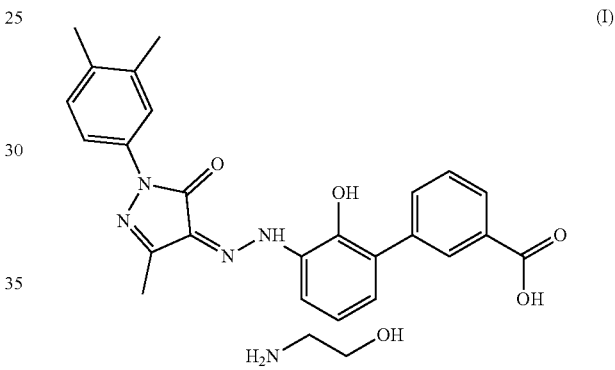

(I)

comprising the following steps:
a) salifying Eltrombopag in a solvent with ammonia to give a crystalline Eltrombopag ammonium salt Form C1 or crystalline Eltrombopag ammonium salt Form C2 or mixture thereof,
b) providing a suspension of the product of the step a) in a solvent and ethanolamine,
c) distilling the mixture of the step b) to give crystalline Eltrombopag monoethanolamine salt Form D of formula (I):

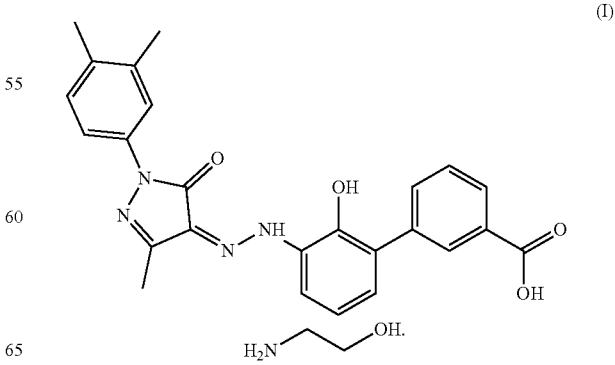

(I)

According to more preferred embodiment of the present invention, in the step a) Eltrombopag is suspended in a solvent.

In the step a) the suspension of Eltrombopag, contains ETP free acid, i.e. Eltrombopag of formula (II):

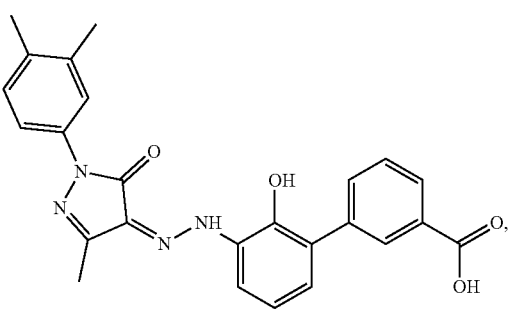

(II)

suspended in a solvent and in presence of ammonia.

Suspension means a solid material suspended in a solution, i.e. mixture of solid Eltrombopag with ammonia is suspended in a solvent, which is liquid. The solvent also contains ammonia.

Ammonia can be aqueous ammonia, ammonium carbonate, ammonia gas, liquid ammonia. Preferably, ammonia in the suspension with ETP of formula (II) in a solvent is aqueous ammonia (30-32% w/w).

Specifically the amount of aqueous ammonia in the step a) is in the range from 1 to 10 molar equivalent. Indeed, said ammonia could be added in excess, for example an amount of ammonia in the range from 3 to 8 molar equivalents, to convert the ETP free acid into ETP ammonium salt.

The starting material ETP free acid is commercially available, for example from Sigma-Aldrich Inc. (USA) with product code COM497515993 and product name Eltrombopag.

Moreover, the above mentioned starting material can be prepared, following the method disclosed in WO 01/89457, specifically, Example 3 describes its preparation.

According to a preferred embodiment of the process of the present invention, the salification of the step a) is carried out at temperature comprised in the range from 20° C. to 50° C.

According to a more preferred embodiment of the process of the present invention, the salification of the step a) is carried out at room temperature or at 40° C.

Room temperature (RT) means a temperature that is comprised in a range of value from 20° C. to 25° C., it is defined as comfortable temperature range indoors.

According to a preferred embodiment of the process of the present invention, the salification of the step a) is carried out in a ketone, alcohol, nitril, ester, aromatic or ether solvent.

Preferably, the solvent can be tetrahydrofuran (THF), Methyl isobutyl ketone (MIBK), Acetonitrile (ACN), Methyl-tert-butyl ether (MTBE), Ethyl acetate (EtOAc), Toluene, Isobutyl acetate (iBuOAc), Isopropyl alcohol (IPA), n-butanol, Ethanol (EtOH) or n-pentanol.

Specifically, the salification of the step a) provides a crystalline Eltrombopag ammonium salt Form C1 or crystalline Eltrombopag ammonium salt Form C2 or mixture thereof, depending on the kind of solvent. In the other words, one or more different solvents can give one or the other form of Eltrombopag ammonium salt, i.e. Form C1 and/or Form C2, or mixture thereof.

The following table (Table 2) shows in the schematic way, the different forms of Eltrombopag ammonium salt, i.e. Form C1 and/or Form C2, or mixture thereof, which are obtained by using different solvents.

TABLE 2

| Entry | T | Solvent | XRPD |
|---|---|---|---|
| 1 | RT | THF | Form C1 |
| 2 | 40° C. | THF | Form C2 |
| 3 | 40° C. | MIBK | Form C2 |
| 4 | | ACN | |
| 5 | | MTBE | |
| 6 | 40° C. | EtOAc | Form C2 |
| 7 | | Toluene | |
| 8 | | iBuOAc | |
| 9 | | IPA | Forms C1 + C2 (traces) |
| 10 | | n-butanol | Forms C1 + C2 |
| 11 | | EtOH | Form C1 + small other peaks |
| 12 | | n-pentanol | Form C1 |

In particular, the Table 2 of the salification of step a) detects the following Eltrombopag ammonium salt forms, when:

the solvent is Methyl isobutyl ketone (MIBK), Acetonitrile (ACN), Methyl-tert-butyl ether (MTBE), Ethyl acetate (EtOAc), Toluene or Isobutyl acetate (iBuOAc), the obtained form is crystalline ETP ammonium salt Form C2 (entry 3 to 8), the solvent is THF at 40° C., the obtained form is ETP ammonium salt Form C2 (entry 2).

the solvent is THF at RT or n-pentanol at 40° C. (entry 1 and 12, respectively), the obtained form is crystalline ETP ammonium salt Form C1.

the solvent is IPA and n-butanol at 40° C., the obtained form is the mixtures thereof (ETP ammonium Form C1 and ETP ammonium Form C2) (entries 9 and 10), the solvent is EtOH at 40° C., the obtained form is ETP ammonium salt Form C1 and non identified peaks (entry 11).

Preferably, the salification of the step a) is carried out in Methyl isobutyl ketone (MIBK), Acetonitrile (ACN), Methyl-tert-butyl ether (MTBE), Ethyl acetate (EtOAc), Toluene or Isobutyl acetate (iBuOAc) to give the crystalline Eltrombopag ammonium salt Form C2, as better described in the experimental part, specifically Example 1 (in MTBE), Example 2 (in EtOAc) and Example 5 (in iBuOAc), and/or in Isopropyl alcohol (IPA) or n-butanol to give the mixture of ETP ammonium salt Form C1 and ETP ammonium salt Form C2.

Moreover, the salification of the step a) is carried out to give the crystalline Eltrombopag ammonium salt Form C1, as better described in the experimental part, specifically Example 3 in n-pentanol.

More preferably, the salification of the step a) is carried out at temperature comprised in the range from 20° C. to 50° C., further preferably is carried out at 40° C., in a Methyl isobutyl ketone (MIBK), Acetonitrile (ACN), Methyl-tert-butyl ether (MTBE), Ethyl acetate (EtOAc), Toluene, Isobutyl acetate (iBuOAc) to give the crystalline Eltrombopag ammonium salt Form C2, and/or in Isopropyl alcohol (IPA) or n-butanol to give the mixture of ETP ammonium salt Form C1 and ETP ammonium salt Form C2.

Alternatively, in the step a) of the process of the present invention, Eltrombopag, i.e. ETP free acid, can be heated to reflux until to reach a complete dissolution. Then, the obtained solution, containing dissolved ETP free acid in a solvent, is salified with ammonia.

Solution means to dissolve a solid compound in a solvent, for example the solution can be as an opalescent solution or a microsuspension or a suspension of little amount of solid material, typically an amount of insoluble material is less than 5% by weight of weight of the compound dissolved in a solvent. In the present invention, the solution is obtained from the dissolution of Eltrombopag.

Specifically, in the present invention the compound in solution is completed dissolved, i.e. Eltrombopag in a solvent produces a limpid solution, without the present of any amount of solid material.

Instead, when Eltrombopag free acid in a solvent is not dissolved completely, the process of the present invention follows the step b) and step c) as slurrying, as described in the Example 4 (in IPA solvent) and Example 5 (in iBuOAc solvent).

In particular, the solvent of the previous step a), wherein ETP free acid is completely dissolved or not dissolved completely, can be Methanol (MeOH), Ethanol (EtOH), Isopropyl alcohol (IPA), n-butanol, n-pentanol, Dioxane, Isobutyl acetate (iBuOAc), tetrahydrofuran (THF) or Ethyl acetate (EtOAc).

Moreover, in the alternative step a) of the present invention, the salification gives a crystalline Eltrombopag ammonium salt Form C1 or crystalline Eltrombopag ammonium salt Form C2 or mixture thereof.

As beforehand described, the following table (Table 3) shows in the schematic way, the different forms of ETP ammonium salt, i.e. Form C1 and/or Form C2, or mixture thereof, which are obtained by different used solvents.

TABLE 3

| Entry | Technique | Solvent | XRPD |
| --- | --- | --- | --- |
| 1 | Slurrying | MeOH | Form C1 |
| 2 | Slurrying | EtOH | |
| 3 | Slurrying | IPA | |
| 4 | Crystallization | n-butanol | |
| 5 | Crystallization | n-pentanol | Form C1 |
| 6 | Crystallization | Dioxane | Form C1 + ETP (traces) |
| 7 | Slurrying | iBuOAc | Form C2 |
| 8 | Crystallization | THF | |
| 9 | Slurrying | EtOAc | Form C2 + small other peaks |

Specifically, the Table 3 of the salification of step a) detects the following Eltrombopag ammonium salt forms, when:
  the solvent is Methanol, Ethanol, Isopropyl alcohol or n-butanol or n-pentanol, the form is crystalline Eltrombopag ammonium salt Form C1,
  the solvent is Dioxane, the form is crystalline Eltrombopag ammonium salt Form C1 and traces of ETP,
  the solvent is Isobutyl acetate or tetrahydrofuran, the form is crystalline Eltrombopag ammonium salt Form C2,
  the solvent is Ethyl acetate, the form is crystalline Eltrombopag ammonium salt Form C2 and traces of other peaks.

According to a preferred embodiment of the process of the present invention, in the step a) the crystalline Eltrombopag ammonium salt Form C1 has characteristic peaks of X-ray powder diffraction pattern expressed in 2-Theta values (2θ) at: 12.5 and 22.5, each peak±0.3, or the crystalline Eltrombopag ammonium salt Form C2 has characteristic peaks of X-ray powder diffraction pattern expressed in 2-Theta values (2θ) at: 14.6, 15.8 and 17.6, each peak±0.3 or the mixture thereof.

According to a more preferred embodiment, the salification of the step a), carried out at temperature comprised in the range from 20° C. to 50° C., in a ketone, alcohol, nitril, ester, aromatic or ethers solvent, gives the crystalline Eltrombopag ammonium salt Form C1, which has characteristic peaks of X-ray powder diffraction pattern expressed in 2-Theta values (2θ) at: 12.5 and 22.5, each peak±0.3, or the crystalline Eltrombopag ammonium salt Form C2, which has characteristic peaks of X-ray powder diffraction pattern expressed in 2-Theta values (2θ) at: 14.6, 15.8 and 17.6, each peak±0.3 or the mixture thereof.

According to a more preferred embodiment, the salification of the step a), carried out at room temperature or at 40° C., in a ketone, alcohol, nitril, ester, aromatic or ethers solvent, gives the crystalline Eltrombopag ammonium salt Form C1, which has characteristic peaks of X-ray powder diffraction pattern expressed in 2-Theta values (2θ) at: 12.5 and 22.5, each peak±0.3, or the crystalline Eltrombopag ammonium salt Form C2, which has characteristic peaks of X-ray powder diffraction pattern expressed in 2-Theta values (2θ) at: 14.6, 15.8 and 17.6, each peak±0.3 or the mixture thereof.

According to preferred embodiment, in the step b) the product of the step a) is suspended in a solvent. Specifically, the crystalline Eltrombopag ammonium salt Form C1 or crystalline Eltrombopag ammonium salt Form C2 or mixture thereof, i.e. one or more of said solid materials are suspended in a solution.

According to a preferred embodiment of the process of the present invention, ethanolamine of the step b) is an amount of one molar equivalent of ethanolamine, compared to ETP.

Molar equivalent means that the molar amount of a substance reacts with a molar amount of another substance in a given chemical reaction.

According to a preferred embodiment of the process of the present invention, the solvent of the step b) is ethyl acetate or toluene.

According to a more preferred embodiment of the process of the present invention, the solvent of the step b) is ethyl acetate.

According to a preferred embodiment, in the step b), the suspension of the product of the step a) is in ethyl acetate and ethanolamine.

According to a more preferred embodiment, in the step b), the suspension of the product of the step a) is in ethyl acetate and an amount of one molar equivalent of ethanolamine, compared to ETP.

According to a preferred embodiment, the salification of the step a) is carried out at temperature comprised in the range from 20° C. to 50° C., in a ketone, alcohol, nitril, ester, aromatic or ether solvent, and provides crystalline Eltrombopag ammonium salt Form C1, which has characteristic peaks of X-ray powder diffraction pattern expressed in 2-Theta values (2θ) at: 12.5 and 22.5, each peak±0.3, or crystalline Eltrombopag ammonium salt Form C2, which has characteristic peaks of X-ray powder diffraction pattern expressed in 2-Theta values (2θ) at: 14.6, 15.8 and 17.6, each peak±0.3 or the mixture thereof, and the solvent of the step b) is ethyl acetate.

According to a more preferred embodiment, the salification of the step a) is carried out at room temperature or at 40° C., in a ketone, alcohol, nitril, ester, aromatic or ether solvent, and gives crystalline Eltrombopag ammonium salt Form C1, which has characteristic peaks of X-ray powder diffraction pattern expressed in 2-Theta values (2θ) at: 12.5 and 22.5, each peak±0.3, or crystalline Eltrombopag ammonium salt Form C2, which has characteristic peaks of X-ray powder diffraction pattern expressed in 2-Theta values (2θ) at: 14.6, 15.8 and 17.6, each peak±0.3 or the mixture thereof, and the solvent of the step b) is ethyl acetate.

According to a preferred embodiment of the process of the present invention, in the step c), the distillation of the mixture of the step b) gives crystalline Eltrombopag monoethanolamine salt Form D of formula (I):

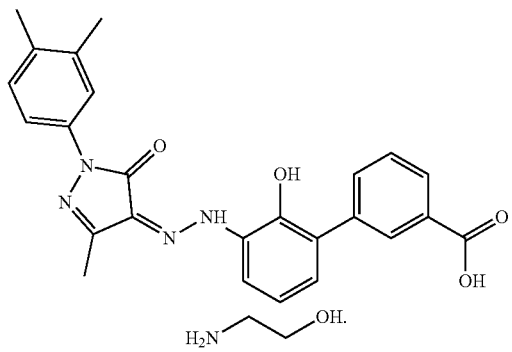

(I)

According to a preferred embodiment, the step c) is carried out by using the same solvent of step b), i.e. is ethyl acetate or toluene.

Preferably, the solvent of the step c) is ethyl acetate.

According to a preferred embodiment, the step c) is carried out by heating to reflux, then by cooling to RT and finally, the resulting suspension is filtered and dried; optionally the step c) can be carried out by using of seed, such as Eltrombopag monoethanolamine salt Form D or Eltrombopag monoethanolamine salt Form H.

According to a preferred embodiment, in the step c), the distillation of the mixture of the step b), which can contain crystalline Eltrombopag ammonium salt Form C1 or crystalline Eltrombopag ammonium salt Form C2 or mixture thereof, in a solvent and ethanolamine, gives crystalline Eltrombopag monoethanolamine salt Form D of formula (I).

According to a more preferred embodiment, in the step c), the distillation of the mixture of the step b), which can contain crystalline Eltrombopag ammonium salt Form C1 or crystalline Eltrombopag ammonium salt Form C2 or mixture thereof, in ethyl acetate or toluene and ethanolamine, gives crystalline Eltrombopag monoethanolamine salt Form D of formula (I).

As above described, the following table (Table 4) shows in the schematic way, the results of the step c).

TABLE 4

| Entry | Starting product | Solvent | Seeding | XRPD |
|---|---|---|---|---|
| 1 | Form C2 | EtOAc | — | Form D |
| 2 | Form C2 + Form C1 (traces) | EtOAc | Form D | Form D |
| 3 | Form C1 | Toluene | Form H | Form D + Form C1 (traces) |
| 4 | Form C2 | Toluene | Form D | Form D + Form C1 (traces) |

According to a more preferred embodiment of the process of the present invention, in the step c), the suspension of Eltrombopag ammonium salt Form C2 in ethyl acetate (EtOAc) and an amount of one molar equivalent of ethanolamine, i.e. mixture of the step b), it is distilled to give crystalline Eltrombopag monoethanolamine salt Form D of formula (I), as described in Example 8:

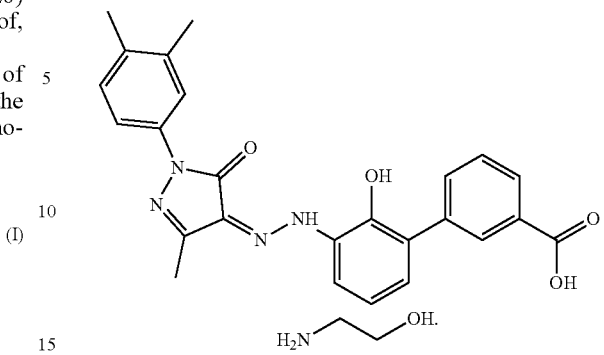

(I)

According to an other preferred embodiment of the process of the present invention, in the step c), the suspension of Eltrombopag ammonium salt Form C1 in Toluene and an amount of one molar equivalent of ethanolamine, i.e. mixture of the step b), it is distilled to give crystalline Eltrombopag monoethanolamine salt Form D of formula (I), as described in Example 10.

Another aspect is thus, the crystalline Eltrombopag ammonium salt Form C1 has characteristic peaks of X-ray powder diffraction pattern expressed in 2-Theta values (2θ) at: 12.5 and 22.5, each peak±0.3.

According to a preferred embodiment, the crystalline Eltrombopag ammonium salt Form C1 has characteristic peaks of X-ray powder diffraction pattern expressed in 2-Theta values (2θ) at: 12.5 and 22.5, each peak±0.2; preferably each peak±0.1.

According to a preferred embodiment, the crystalline Eltrombopag ammonium salt Form C1 has characteristic peaks of X-ray powder diffraction pattern expressed in 2-Theta values (2θ) at: 5.0, 10.4, 12.5, 22.5 and 24.4, each peak±0.3.

Moreover, the list of the values of the peaks of X-powder diffraction ray pattern expressed in 2-Theta values (2θ) of the crystalline ETP ammonium salt Form C1 is reported in the following Table 5, which refers to FIG. 3:

TABLE 5

| Pos. [° 2θ] | d-spacing [Å] | Rel. Int. [%] |
|---|---|---|
| 5.0 | 17.7 | 24 |
| 6.3 | 14.1 | 100 |
| 6.9 | 12.7 | 11 |
| 9.0 | 9.8 | 6 |
| 10.4 | 8.5 | 25 |
| 12.2 | 7.2 | 16 |
| 12.5 | 7.1 | 10 |
| 13.2 | 6.7 | 3 |
| 13.9 | 6.4 | 2 |
| 14.8 | 6.0 | 20 |
| 15.1 | 5.9 | 9 |
| 18.1 | 4.9 | 5 |
| 19.6 | 4.5 | 1 |
| 20.2 | 4.4 | 1 |
| 20.8 | 4.3 | 1 |
| 22.5 | 4.0 | 10 |
| 24.4 | 3.7 | 11 |
| 25.3 | 3.5 | 1 |
| 26.0 | 3.4 | 1 |
| 27.0 | 3.3 | 3 |
| 27.7 | 3.2 | 4 |

According to a preferred embodiment, the crystalline Eltrombopag ammonium salt Form C1 has DSC onset comprised in the range from 170° C. to 174° C. as measured by DSC.

The onset value corresponds to the melting point recorded by DSC analysis, whose method is better described in the experimental part.

According to more preferred embodiment of the present invention, the crystalline Eltrombopag ammonium salt Form C1 has onset about 172° C. as measured by DSC.

According to a preferred embodiment, the crystalline Eltrombopag ammonium salt Form C1 has peak in the range from 195° C. to 199° C., specifically, about 197° C. as measured by DSC.

According to a preferred embodiment, the crystalline Eltrombopag ammonium salt Form C1 has onset about 172° C. and peak at about 197° C., as measured by DSC.

Figure 5:
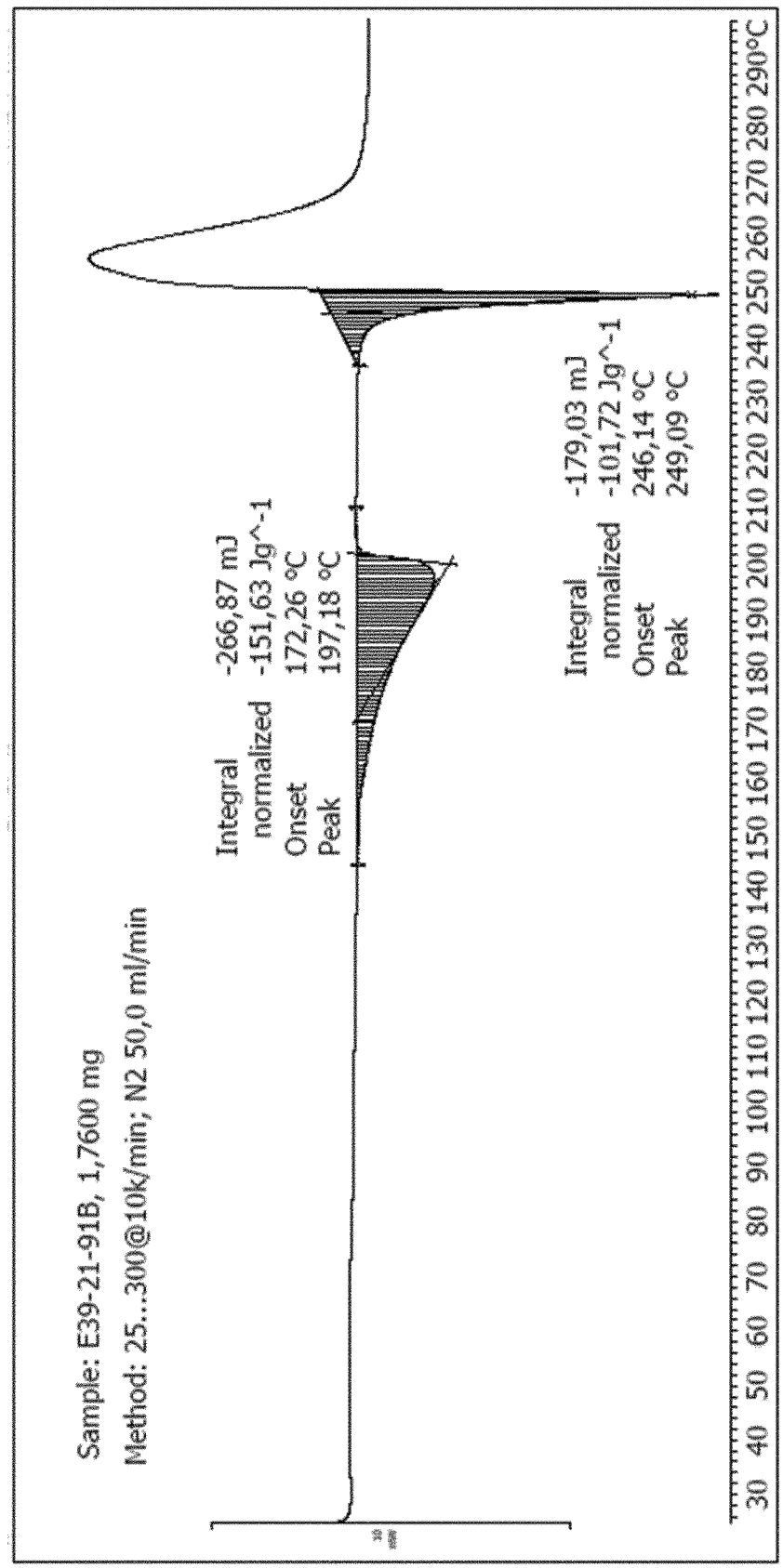
FIG. 5 shows the DSC curve of ETP ammonium salt Form C1.

Said DSC analysis shows two endothermic events, specifically, the main endothermic event of Eltrombopag ammonium salt Form C1 with an onset at 172° C. and a peak at 197° C., and the second curve has an onset at 246° C. and a peak at 249° C., as shown in FIG. 5.

Another aspect is thus, the crystalline Eltrombopag ammonium salt Form C2 has characteristic peaks of X-ray powder diffraction pattern expressed in 2-Theta values (2θ) at: 14.6, 15.8 and 17.6, each peak±0.3.

According to a preferred embodiment, the crystalline Eltrombopag ammonium salt Form C2 has characteristic peaks of X-ray powder diffraction pattern expressed in 2-Theta values (2θ) at: 14.6, 15.8 and 17.6, each peak±0.2; preferably each peak±0.1.

Figure 4:
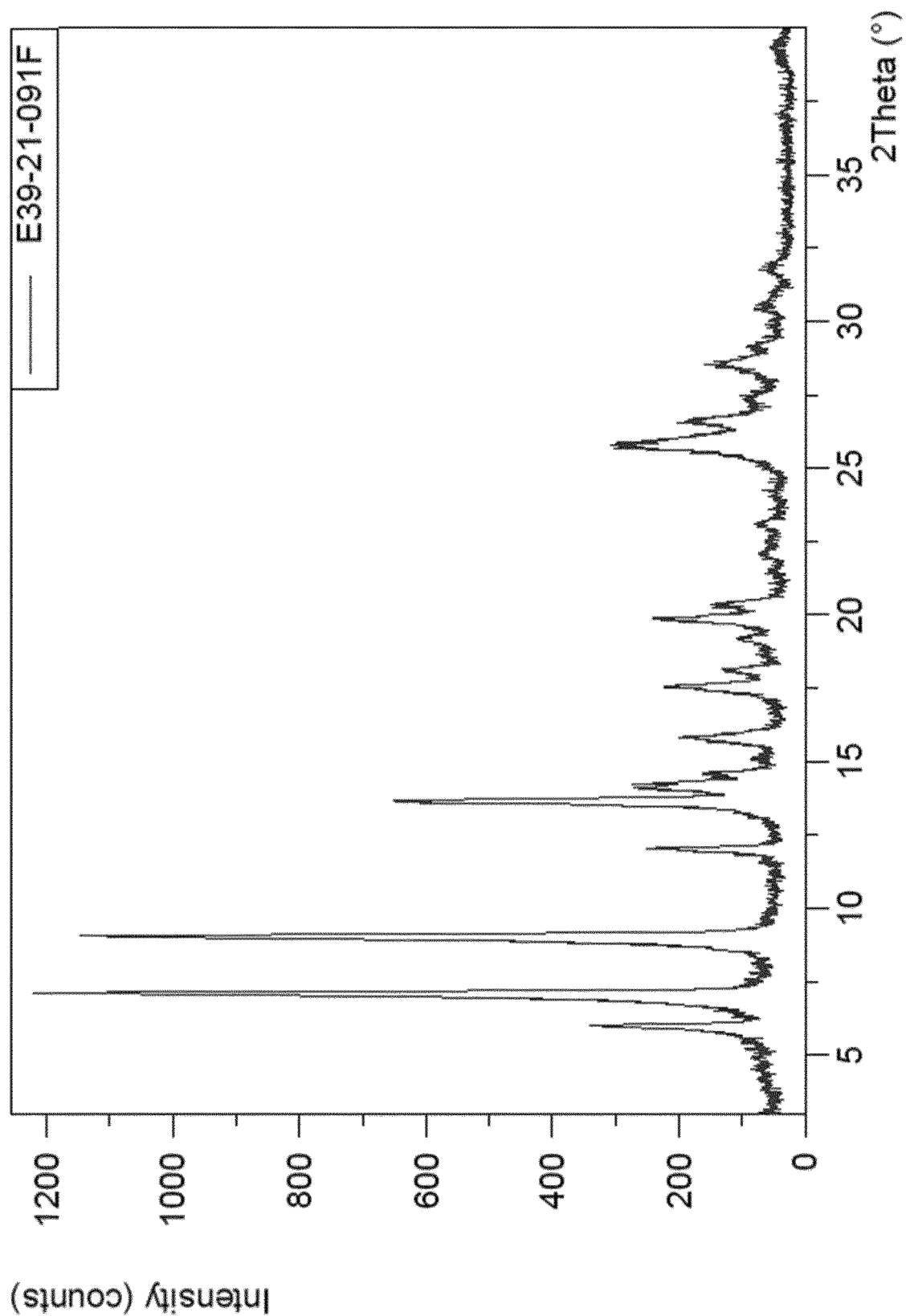
FIG. 4 shows the powder x-ray diffraction pattern of ETP ammonium salt Form C2, obtained by the step a) of the process of the present invention.

Moreover, the list of the values of the peaks of X-ray powder diffraction ray pattern expressed in 2-Theta values (2θ) of the crystalline ETP ammonium salt Form C2 is following reported in Table 6, which refers to FIG. 4.

TABLE 6

| Pos. [° 2θ] | d-spacing [Å] | Rel. Int. [%] |
|---|---|---|
| 6.0 | 14.7 | 25 |
| 7.1 | 12.4 | 90 |
| 9.1 | 9.8 | 100 |
| 12.0 | 7.3 | 18 |
| 13.6 | 6.5 | 57 |
| 14.1 | 6.3 | 17 |
| 14.6 | 6.1 | 8 |
| 15.8 | 5.6 | 13 |
| 17.6 | 5.0 | 15 |
| 18.2 | 4.9 | 7 |
| 19.2 | 4.6 | 4 |
| 19.9 | 4.5 | 17 |
| 20.4 | 4.3 | 8 |
| 22.1 | 4.0 | 2 |
| 23.1 | 3.9 | 3 |
| 25.7 | 3.5 | 21 |
| 26.6 | 3.3 | 11 |
| 27.4 | 3.3 | 3 |
| 28.5 | 3.1 | 8 |
| 29.2 | 3.1 | 3 |
| 30.5 | 2.9 | 2 |
| 31.8 | 2.8 | 2 |

Another aspect of the present invention is thus, the use of the crystalline Eltrombopag ammonium salt Form C1 or crystalline Eltrombopag ammonium salt Form C2 as above described for preparing crystalline Eltrombopag monoethanolamine salt Form D as the product of the present invention.

Specifically, the process of preparation of crystalline Eltrombopag monoethanolamine salt Form D passes through the crystalline Eltrombopag ammonium salt Form C1 or crystalline Eltrombopag ammonium salt Form C2.

In particular, a suspension of Eltrombopag ammonium salt Form C1 or crystalline Eltrombopag ammonium salt Form C2 in a solvent and ethanolamine is provided, as described in the step b) of the process. Then, the mixture of the step b) is distilled to give crystalline Eltrombopag monoethanolamine salt Form D of formula (I).

According to a more preferred embodiment, a suspension of Eltrombopag ammonium salt Form C1 or crystalline Eltrombopag ammonium salt Form C2 in ethyl acetate and an amount of one molar equivalent of ethanolamine is provided, as described in the step b) of the process. Then, the mixture of the step b) in ethyl acetate is distilled to give crystalline Eltrombopag monoethanolamine salt Form D of formula (I).

Another aspect is thus, a pharmaceutical composition comprises a crystalline Eltrombopag monoethanolamine salt Form D as above described, and one or more pharmaceutically acceptable excipients.

Indeed, said crystalline form of Eltrombopag monoethanolamine salt Form D is well stable and well suitable to be employed for pharmaceutical purposes, as show in the Example 17, which refers to stability study.

Moreover, a pharmaceutical composition can comprise a crystalline Eltrombopag monoethanolamine salt Form D in combination with a polymorphs of Eltrombopag bisethanolamine and one or more pharmaceutically acceptable excipients.

Pharmaceutical compositions have different dosage forms, which may include, for example, capsules, tablets, powders, suspensions or any other suitable dosage form. In such said dosage forms, Eltrombopag monoethanolamine salt Form (I) may be combined with one or more pharmaceutically acceptable excipients, carriers or diluents, such as, for example mannitol, silicic derivatives or sugar.

Another aspect of the present invention is thus, a crystalline Eltrombopag monoethanolamine salt Form D as above described or the pharmaceutical composition as beforehand discussed, for use as medicament.

Further aspect of the present invention is thus, a crystalline Eltrombopag monoethanolamine salt Form D as above described or the pharmaceutical composition as beforehand discussed, for the treatment of chronic immune thrombocytopenia.

According to a preferred embodiment, a crystalline Eltrombopag monoethanolamine salt Form D as above described or the pharmaceutical composition as beforehand discussed, can be used for the treatment of adults and children 1 years of age older with chronic immune thrombocytopenia.

Finally, considering that ETP monoethanolamine salt Form E is not stable, and therefore is discharged for pharmaceutical purposes (see example 14), the crystalline Eltrombopag monoethanolamine salt Form D has the best non-hygroscopic behaviour compared to known ETP monoethanolamine salt Form H, the highest solubility in water and good thermodynamic stability, therefore it is advantageously suitable for pharmaceutical purposes.

EXPERIMENTAL SECTION

The starting material Eltrombopag free acid can be prepared according to known prior art methods, for example, as described in in WO 01/89457 or can be purchased on the market (for exp. Sigma Aldrich).

The following table lists the abbreviations used:

| | |
|---|---|
| ACN | Acetonitrile |
| °C. | Degree Centigrade or Degree Celsius |
| DSC | Differential scanning calorimetry |
| DVS | Dynamic Vapour Sorption |
| EA | Ethanolamine |
| EtOAc | Ethyl acetate |
| eq. | Equivalent |
| G | Gramme |
| h | Hour |
| HPLC | High performance liquid chromatography |
| IPA | Isopropyl alcohol |
| min | minute |
| mg | Milligramme |
| mL | Millilitre |
| mmol | Millimole |
| MTBE | Methyl-tert-butyl ether or tert-butyl methyl ether |
| RH | relative humidity |
| rpm | revolutions per minute |
| RT | Room temperature |
| T | Temperature |
| THF | Tetrahydrofuran |
| V | Volume |
| w/w | Weight/weight |
| XPRD | X-ray Powder Diffraction |
| μL | Microlitre |

Example 1: Process for the Preparation of the Crystalline Eltrombopag Ammonium Salt Form C2, in MTBE Solvent According to the Step a). (Reported in the Table 2, Entry 5)

To an assay tube equipped with magnetic stirring, containing a suspension of ETP free acid (0.07 mmol) in TBME (0.62 mL, 17 V) at 40° C., was added aqueous ammonia 32% w/w (35 μL, 0.6 mmol, 8 eq.) before stirring for 1 h at 40° C. and 1 h at 0-5° C. The resulting suspension was centrifuged at 0° C. (14000 rpm-2 min) in order to isolate the solid. After drying at RT under vacuum, the crystalline Eltrombopag ammonium salt Form C2 was obtained according to XRPD analysis (shown FIG. 4).

Example 2: Process for the Preparation of the Crystalline Eltrombopag Ammonium Salt Form C2, in EtOAc Solvent According to the Step a). (Reported in the Table 2, Entry 6)

To an assay tube equipped with magnetic stirring, containing a suspension of ETP free acid (0.07 mmol) in EtOAc (0.65 mL, 17 V) at 40° C., was added aqueous ammonia 32% w/w (35 μL, 0.6 mmol, 8 eq.) before stirring for 1 h at 40° C. and 1 h at 0-5° C. The resulting suspension was centrifuged at 0° C. (14000 rpm-2 min) in order to isolate the solid. After drying at RT under vacuum, the crystalline Eltrombopag ammonium salt Form C2 was obtained according to XRPD analysis, which is equivalent to XRPD analysis of the FIG. 4.

Example 3: Process for the Preparation of the Crystalline Eltrombopag Ammonium Salt Form C1, in 1-Pentanol Solvent According to the Step a). (Reported in the Table 2, Entry 12)

To an assay tube equipped with magnetic stirring, containing a suspension of ETP free acid (0.07 mmol) in 1-pentanol (0.65 mL, 17 V) at 40° C., was added aqueous ammonia 32% w/w (35 μL, 0.6 mmol, 8 eq.) before stirring for 1 h at 40° C. and 1 h at 0-5° C. The resulting suspension was centrifuged at 0° C. (14000 rpm-2 min) in order to isolate the solid. After drying at RT under vacuum, the crystalline Eltrombopag ammonium salt Form C1 was obtained according to XRPD analysis. (shown FIG. 3).

Example 4: Process for the Preparation of the Crystalline Eltrombopag Ammonium Salt Form C1, in IPA Solvent According to the Step a). (Reported in the Table 3, Entry 3)

To an assay tube equipped with magnetic stirring, containing a suspension of ETP free acid (0.07 mmol) in IPA (1 mL, 27 V) at reflux, was added slowly IPA. After 3 mL IPA addition, complete dissolution was not observed. To the resulting suspension, aqueous ammonia 32% w/w (35 μL, 0.6 mmol, 8 eq.) was added before cooling to RT. After 1 h stirring at RT and 1 h at 0-5° C., the resulting suspension was centrifuged at 0° C. (14000 rpm-2 min) in order to isolate the solid. After drying at RT under vacuum, the crystalline Eltrombopag ammonium salt Form C1 was obtained according to XRPD analysis, that is equivalent to XRPD analysis of the FIG. 3.

Example 5: Process for the Preparation of the Crystalline Eltrombopag Ammonium Salt Form C2, in iBuOAc Solvent According to the Step a). (Reported in the Table 3, Entry 7)

To an assay tube equipped with magnetic stirring, containing a suspension of ETP free acid (0.07 mmol) in iBuOAc (1 mL, 27 V) at reflux, was added slowly iBuOAc. After 3 mL iBuOAc addition, complete dissolution was not observed. To the resulting suspension, aqueous ammonia 32% w/w (35 μL, 0.6 mmol, 8 eq.) was added before cooling to RT. After 1 h stirring at RT and 1 h at 0-5° C., the resulting suspension was centrifuged at 0° C. (14000 rpm-2 min) in order to isolate the solid. After drying at RT under vacuum, ETP ammonium salt Form C2 was obtained according to XRPD analysis, which is equivalent to XRPD analysis of the FIG. 4.

Example 6: Process for the Preparation of the Crystalline Eltrombopag Ammonium Salt Form C1 by Crystallisation in n-Butanol. (Reported in the Table 3, Entry 4)

To a glass test tube equipped with magnetic stirring, ETP free acid (0.07 mmol) and 1-butanol (1 ml, 27 V) were added. The suspension was heated to reflux until a complete dissolution was obtained, before adding 32% w/w aqueous ammonia (35 μL, 0.6 mmol, ca. 8 eq.). Precipitation was immediately observed. The mixture was allowed to cool down, stirred for 1 h at RT, and 1 h at 0-5° C. The resulting brown-reddish suspension was centrifuged at 0° C. (14000 rpm—2 min) in order to isolate the solid. After drying at RT under vacuum, ETP ammonium salt Form C1 was obtained according to XRPD analysis, which is equivalent to XRPD analysis of the FIG. 3.

Example 7: Process for the Preparation of the Crystalline Eltrombopag Ammonium Salt Form C2 by Crystallisation in THF. (Reported in the Table 3, Entry 8)

To a glass test tube equipped with magnetic stirring, ETP free acid (0.07 mmol) and THF (1 ml, 27 V) were added. The mixture was heated to reflux until complete dissolution was obtained, before adding 32% w/w aqueous ammonia (35 µL, 0.6 mmol, ca. 8 eq.). An immediate precipitation was observed. The mixture was allowed to cool down, stirred for 1 h at RT, and 1 h at 0–5° C. The resulting brown-reddish suspension was centrifuged at 0° C. (14000 rpm-2 min) in order to isolate the solid. After drying at RT under vacuum, ETP ammonium salt Form C2 was obtained according to XRPD analysis, which is equivalent to XRPD analysis of the FIG. 4.

Example 8: Process for the Preparation of Eltrombopag Monoethanolamine Salt Form D of Formula (I) Starting from Crystalline Eltrombopag Ammonium Salt Form C2, in EtOAc Solvent Following the Step b) and c) of Present Invention

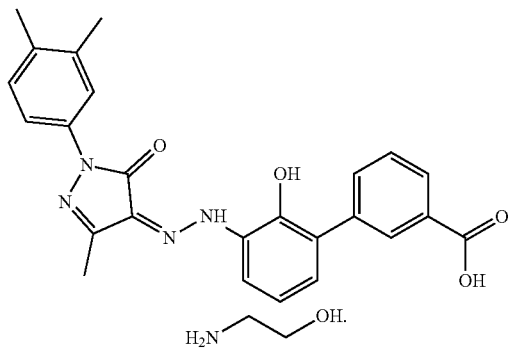

To a round-bottomed flask equipped with magnetic, stirring and a distillation apparatus containing ETP ammonium salt Form C2 (35 mg, 0.08 mmol) in suspension in EtOAc (10.3 ml, 290 V), was added ethanolamine (5 µl, 5.1 mg, 0.08 mmol, 1 eq). The resulting suspension was heated to reflux in order to distil partially the solvent: about 5 ml of solvent were initially distilled before adding EtOAc (5 ml), and continuing the distillation to obtain a total of 10 ml of distilled solvent. The crude (a brown-yellowish suspension) was cooled to RT before filtering and washing with EtOAc (2×1 ml). After drying at RT under vacuum, Eltrombopag monoethanolamine salt Form D of formula (I) (29.2 mg, 76%) was obtained according to XRPD analysis of the FIG. 1. (Reported in the Table 4, Entry 1).

Example 9: Process for the Preparation of Eltrombopag Monoethanolamine Salt Form D of Formula (I), Starting from Crystalline Eltrombopag Ammonium Salt Form C2, in EtOAc Solvent and Using Seed Following the Step b) and c) of Present Invention. (Reported in the Table 4, Entry 2)

To a round-bottomed flask equipped with magnetic, stirring and a distillation apparatus containing ETP ammonium salt Form C2 and traces of Form C1 (115 mg, 0.25 mmol) in suspension in EtOAc (10 ml, 90 V), were added. The mixture was seeded (i.e. with ETP monoethanolamine salt Form D, whose process for the preparation is beforehand described) at RT with Form D (about 0.5-1 mg) and then ethanolamine (15 µl, 15 mg, 0.25 mmol, 1 eq) was added. The resulting suspension was heated to reflux in order to distil partially the solvent: about 5 ml of solvent were initially distilled, before adding EtOAc (5 ml) and continuing the distillation to obtain a total of 10 ml of distilled solvent. The brown-yellowish suspension was cooled to RT before filtering and washing with EtOAc (2×1 ml). After drying at RT under vacuum, Eltrombopag monoethanolamine salt Form D (107 mg, 85%) was obtained according to XRPD analysis, which is equivalent to XRPD analysis of the FIG. 1.

Example 10: Process for the Preparation of Eltrombopag Monoethanolamine Salt Form D of Formula (I), Starting from Crystalline Eltrombopag Ammonium Salt Form C1, in Toluene Solvent and Using Seed Form H Following the Step b) and c) of Present Invention. (Reported in the Table 4, Entry 3)

To a round-bottomed flask, equipped with magnetic stirring and a distillation apparatus, ETP ammonium salt Form 01 (38 mg, 0.08 mmol) and toluene (10 ml, 270 V) were added. The suspension was seeded at RT with Form H (whose preparation is described in background of the present invention) (about 0.5-1 mg) and then ethanolamine (5 µL, 5 mg, 0.08 mmol, 1 eq) was added. The resulting suspension was heated to reflux in order to distil partially the solvent: about 5 ml of solvent were distilled. The brown-yellowish suspension was cooled to RT before filtering and washing with toluene (2×1 ml). After drying at RT under vacuum, Eltrombopag monoethanolamine salt Form D (40 mg, 94%) with traces of the starting ETP ammonium salt Form C1 were obtained, according to XRPD analysis, which respectively are equivalent to XRPD analysis of the FIG. 1 and FIG. 3.

Example 11: Process for the Preparation of Eltrombopag Monoethanolamine Salt

Form D of formula (I), starting from crystalline Eltrombopag ammonium salt Form C2, in Toluene solvent and using seed Form D following the step b) and c) of present invention. (Reported in the Table 4, Entry 4).

To a round-bottomed flask, equipped with magnetic stirring and a distillation apparatus, ETP ammonium salt Form C2 (115 mg, 0.25 mmol) and toluene (10 ml, 90 V) were added. The mixture was seeded at RT with Form D (ca. 0.5-1 mg) and then ethanolamine (15 µL, 15 mg, 0.25 mmol, 1 eq) was added. The resulting suspension was heated to reflux in order to distil partially the solvent: about 5 ml of solvent were initially distilled before adding toluene (5 ml) and continuing the distillation to obtain a total of 10 ml of distilled solvent. The brown-yellowish suspension was cooled to RT before filtering and washing with toluene (2×1 ml). After drying at RT under vacuum, ETP monoethanolamine salt Form D (101 mg, 80%) with traces of ETP ammonium salt Form C1 was obtained according to XRPD analysis, which respectively are equivalent to XRPD analysis of the FIG. 1 and FIG. 3.

Example 12: XPRD Diffractometer and Method for the Characterization of the Following Products of the Present Invention Diffraction measurements were performed at ambient conditions on a PANalytical X'Pert PRO 2 theta (2θ) diffractometer of 240 mm of radius in reflection geometry, equipped with Cu Kα radiation and a PIXcel detector, operated at 45 kV and 40 mA.

Each sample was mounted on a zero-background silicon holder and allowed to spin at 0.25 rev/s during the data collection. The measurement angular range was 3.0-40.0° (2θ) with a step size of 0.013°. The scanning speed was 0.0328°/s for routine analysis and 0.082°/s for characterization and final product analysis.

XPRD Diffractogram of the Crystalline Eltrombopag Monoethanolamine Salt Form D of formula (I):

Said compound prepared, as described in the previous examples (i.e. as in example 8), was analyzed and the XRPD diffractogram, as disclosed in the description part of the invention, and showed in FIG. 1.

In particular, the crystalline Eltrombopag monoethanolamine salt Form D (I) has one of the following characteristic peaks of X-ray powder diffraction pattern expressed in 2-Theta values (2θ) at: 7.8, 11.1 and 19.1, each peak±0.2.

Figure 3:
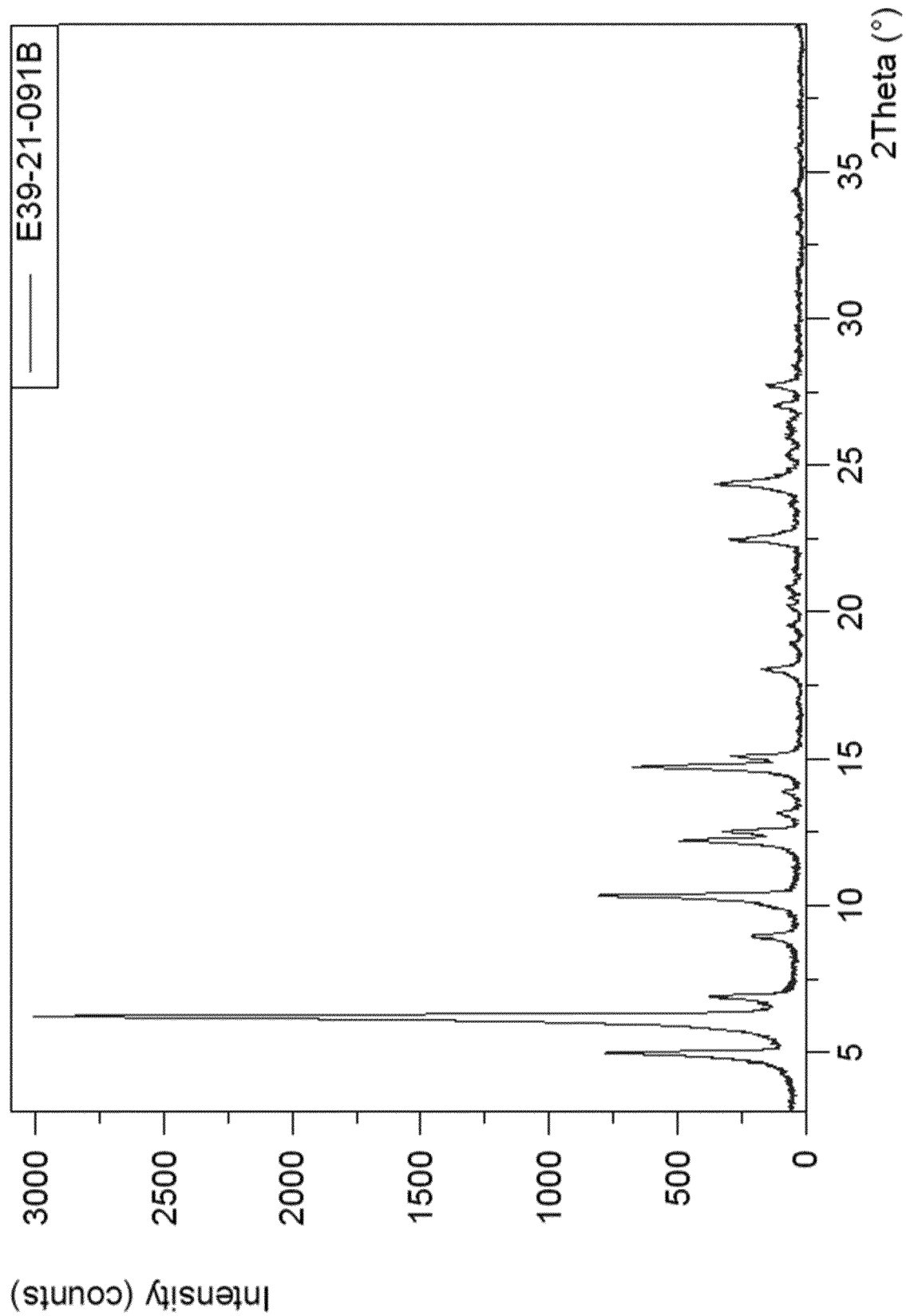
FIG. 3 shows the powder x-ray diffraction pattern of ETP ammonium salt Form C1, obtained by the step a) of the process of the present invention.

XPRD Diffractogram of the Crystalline Eltrombopag Ammonium Salt Form C1:

The crystalline Eltrombopag ammonium salt Form C1 prepared as described in the previous examples (i.e. as in example 4), was analysed and the XRPD diffractogram, as beforehand described, and showed in FIG. 3.

In particular, the crystalline Eltrombopag ammonium salt Form C1 has characteristic peaks of X-ray powder diffraction pattern expressed in 2-Theta values (2θ) at: 12.5 and 22.5, each peak±0.3.

XPRD Diffractogram of the Crystalline Eltrombopag Ammonium Salt Form C2:

The crystalline Eltrombopag ammonium salt Form C2 prepared as described in the previous examples (i.e. as in example 1) was analyzed and the XRPD diffractogram, as beforehand described, and showed in FIG. 4.

In particular, the crystalline Eltrombopag ammonium salt Form C2 has characteristic peaks of X-ray powder diffraction pattern expressed in 2-Theta values (2θ) at: 14.6, 15.8 and 17.6, each peak±0.3.

Example 13: DSC

DSC analyses were recorded with a Mettler Toledo DSC2. Samples were weighed into a 40 µL aluminium crucible with a pinhole lid and heated at 10K/min from 25 to 300° C. under nitrogen (50 mL/min).

DSC analysis of the crystalline Eltrombopag monoethanolamine salt Form D of formula (I):

1.2800 mg of sample of Eltrombopag monoethanolamine salt Form D were analysed by DSC.

Said DSC analysis shows one endothermic event with an onset at 232° C. that corresponds to the melting of ETP monoethanolamine salt Form D and a peak at 238° C., followed by a large exothermic event due to a degradation event (as shown in FIG. 2).

DSC Analysis of the Crystalline Eltrombopag Ammonium Salt Form C1:

DSC analysis shows two endothermic events (as shown in FIG. 3):
the first has an onset at 172° C. that corresponds to the melting of ETP ammonium salt Form C1 and peak at 197° C., followed by a large exothermic event due to a degradation event,
the second has an onset at 246° C. and peak at 249° C., followed by a large exothermic event due to a degradation event.

DSC Analysis of the Eltrombopag Monoethanolamine Salt Form H:

1.2500 mg of sample of Eltrombopag monoethanolamine salt Form H were analysed by DSC.

DSC analysis shows two endothermic events:
the first having an onset at about 199° C. and a peak at 215° C.
the second having an onset at about 234.9° C. and a peak at 239.2° C.

In particular, the first endothermic event, with an onset at about 199° C., corresponds to a polymorphic transition of ETP monoethanolamine salt Form H to another crystalline form, specifically crystalline Eltrombopag monoethanolamine salt Form D1, as provided by XPRD diffractogram; and following the second endothermic event, with an onset at about 234.9° C., corresponds to the melting of this crystalline Eltrombopag monoethanolamine salt Form D1 (as shown in FIG. 6).

DSC Analysis of the Crystalline Eltrombopag Monoethanolamine Salt Form D1:

DSC analysis shows only one endothermic event with an onset at 235° C., which corresponds to the melting of Eltrombopag monoethanolamine salt Form D1, and a peak at 239° C. (as shown in FIG. 7).

This one endothermic event is an evidence of the own stability of said crystalline Eltrombopag monoethanolamine salt Form D1.

Example 14: Stability Study of Eltrombopag Monoethanolamine Salt Form E

The stability of Eltrombopag monoethanolamine salt Form E, whose preparation is described in background of the present invention, was carried out following two different conditions.

In the first ETP monoethanolamine salt Form E was exposed to atmospheric conditions for 1 day was unstable, and a new form very similar to Form II (ETP bisethanolamine salt) described in U.S. Pat. No. 8,372,822B2 was recovered according to XRPD analysis.

In the second ETP monoethanolamine salt Form E was exposed to ICH guideline accelerated conditions (40° C./75 RH %). Under these conditions, Form E converted partially to a new unknown form.

Results of stability study after 1 day of exposition:
1) Atmospheric conditions: Form II+ one peak at 8.6° (2θ),
2) 40° C./75 RH %: partial conversion to a new form with a main peak at 8.6° (2θ).

Therefore, ETP monoethanolamine salt Form E is not stable under atmospheric or ICH guideline accelerated conditions for 1 day, and therefore not suitable for pharmaceutical purpose.

Example 15: Hygroscopicity Study of Various Crystalline Eltrombopag Monoethanolamine Salt Forms: ETP Monoethanolamine Salt Form D, ETP Monoethanolamine Salt Form H, ETP Monoethanolamine Salt Form D1, ETP Monoethanolamine Salt Form H2

Hygroscopicity study was determined by DVS (Dynamic Vapour Sorption) with a Q5000 TA instrument. This is a gravimetric technique that measures how much water is absorbed or desorbed by a sample at different relative humidity (RH). At each RH, the sample mass must be allowed to reach gravimetric equilibrium (or surpassed time limit) before progressing to the next humidity level. Sorption and desorption isotherms were performed at 25° C. over a range of 0-95% RH.

The samples gently milled were not previously dried but they were exposed to 0% RH until a stable weight was reached before starting the DVS cycle. This equilibration step allows possible adsorbed humidity to be eliminated.

DVS analyses were performed with ca. 10 mg of the 4 crystalline ETP monoethanolamine salt forms (Form D, Form H, Form D1 and Form H2) following the conditions described below:

weight equilibration at 25° C. under 0% RH, increase to the higher RH % level when the weigh variation of the sample is inferior to 0.02% w/w after 10 min or after a time limit of 300 min.

Figure 8:
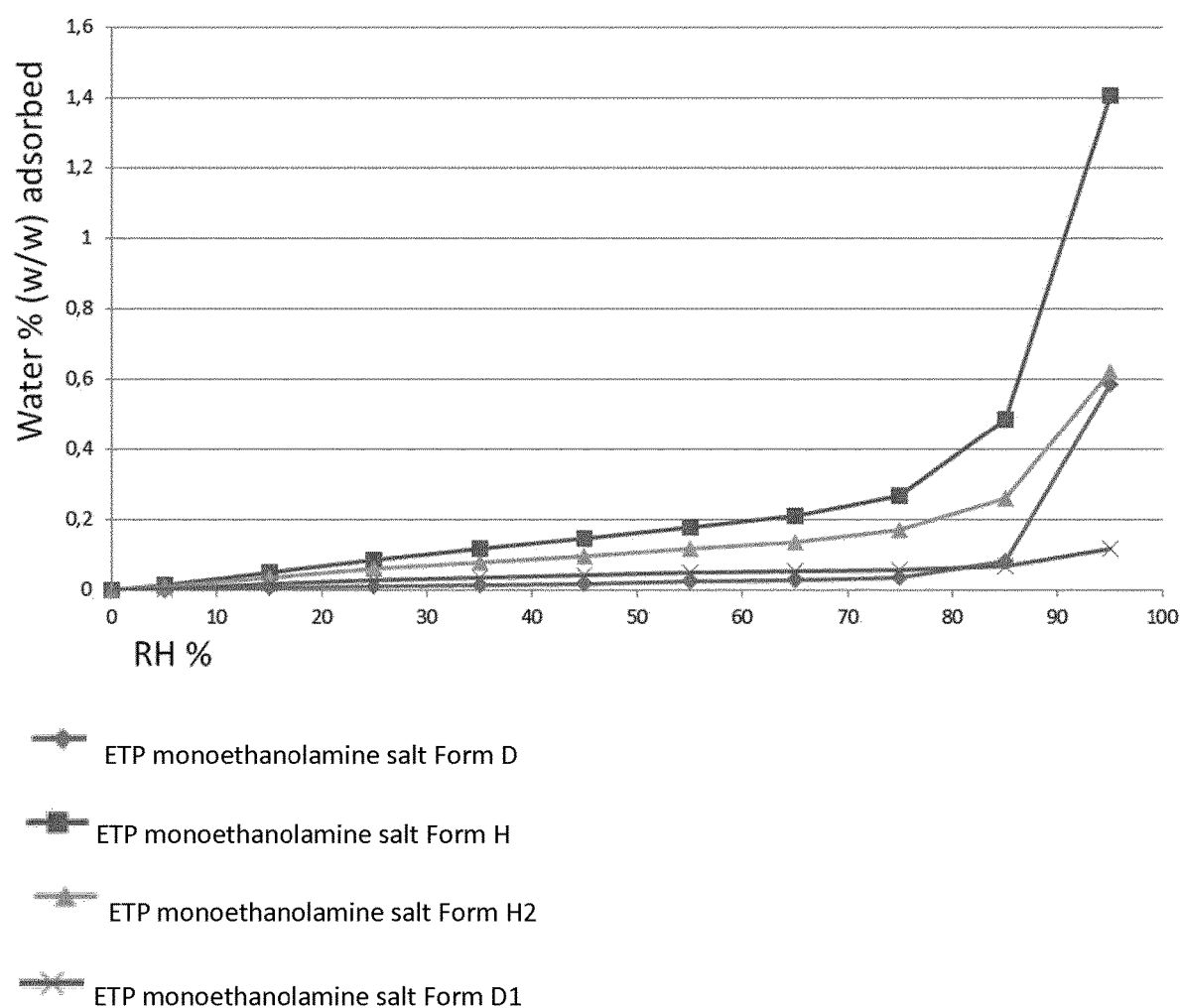
FIG. 8 shows the humidity adsorption curves of four ETP monoethanolamine salt forms, described in the example 15.

A graphic comparison of the humidity absorption profile of the 4 forms is shown on FIG. 8.

DVS analysis of the different monoethanolamine salts indicated that the water uptake increases progressively between 0 and 85% RH before increasing faster at 95% RH. However, the final water uptake remains low indicating that these forms are slightly hygroscopic (up to 1.4% w/w at 95% RH).

a. ETP monoethanolamine salt Form H is the most hygroscopic form, adsorbing up to 1.4% w/w of humidity at 95% RH.

b. ETP monoethanolamine salt Form H2, unknown in literature, is a form similar to ETP monoethanolamine salt Form H. Said ETP monoethanolamine salt Form H2 has a hygroscopicity similar to Form H up to 85% RH, but remained lower at 95% RH (0.6 vs 1.4 w/w).

c. ETP monoethanolamine salt Form D is not hygroscopic up to 85% RH.

The solids recovered after the DVS analysis cycle maintained their initial crystalline form according to XRPD (crystalline conversion did not occur).

Therefore, ETP monoethanolamine salt Form D shows a lower hygroscopitiy respect to Form H, previously described in the literature.

Therefore, ETP monoethanolamine salt Form D has a better hygroscopicity than ETP monoethanolamine salt Form H and unknown Form H2.

Example 16: Water Solubility Study of Different Crystalline Eltrombopag Monoethanolamine Salt Forms: ETP Monoethanolamine Salt Form D, ETP Monoethanolamine Salt Form H, ETP Monoethanolamine Salt Form D1, ETP Monoethanolamine Salt Form H2

The relative solubility of the above mentioned 4 ETP monoethanolamine salt Forms was studied in water at RT. The validity of any solubility measurement requires that the crystalline form must remain stable with respect to any phase conversion taking place during the determination of the equilibrium solubility.

Preliminary Stability in Water

A preliminary test stability study in water at RT of 4 ETP monoethanolamine salt Forms was performed in order to observed possible crystalline transitions.

A sample of each crystalline form was slurried in water at RT and periodically analysed by XRPD (1, 3, 6 and 24 h) in order to detect possible crystalline transformation.

ETP monoethanolamine salt Form D, Form H, Form D1 and Form H2 remained stable 24 h under these conditions. Then, their thermodynamic solubility can be determined.

Determination of Relative Thermodynamic Solubility in Water at RT by HPLC

Once confirmed that the different ETP monoethanolamine forms are stable under water, the thermodynamic solubility of these forms was evaluated.

As the solubility of these forms was very low in water, a suspension (10 mg in 1 mL of water) was performed in water at RT in order to afford a saturated solution. This suspension was stirred 24 h at RT in order to reach the equilibrium. Then, a sample was filtered and the resulting filtrate was analysed by HPLC by duplicate. The average peak area of ETP gave a relative value of the thermodynamic solubility of each form that can be compared with each other. The solids recovered after filtration were also analysed by XRPD to check that no crystalline phase transformation occurred during the slurring.

The following HPLC conditions were used to determine the relative solubility (due to their short analysis time and good response):

Column: C18 Zorbax Eclipse (XDB), 150×4.6 mm, 5 μm
Sample concentration: Saturated water solution of the ETP monoethanolamine salt
Mobile phase: ACN:MeOH:H2O (55:35:10) at pH=6.0+/− 0.2
Temperature: 27° C.
Flow rate: 1 mL/min
UV detector wavelength: 230 nm
Injection: 5 μL
Run time: 10 min HPLC ETP peak area in each of the different forms analysed was measured in order to establish their relative solubility. The HPLC analyses were performed by duplicate for each ETP monoethanolamine salt. This solubility study was repeated twice in order to confirm the solubility values, as reported in the following Table 7).

TABLE 7

| Entry | Form | Solubility test #1 (area counts) | Solubility test #2 (area counts) | Intensity test average | Standard deviation |
|---|---|---|---|---|---|
| 1 | Form D | 7930 | 8201 | 8066 | 192 |
| 2 | Form H | 3963 | 5031 | 4497 | 755 |
| 3 | Form D1 | 2722 | 3100 | 2911 | 267 |
| 4 | Form H2 | 3068 | 2665 | 2867 | 285 |

ETP monoethanolamine salt Form D was the most soluble from as shown by the solubility tests with the highest peak area (Entry 1). Therefore, Form D is the most soluble form in water at RT.

ETP monoethanolamine salt Form H afforded a relative solubility intermediate (Entry 2).

Then, ETP monoethanolamine salt Form D has the best solubility in water.

Thus, ETP monoethanolamine salt Form D can be conveniently employed for the preparation of fast-release pharmaceutical compositions of ETP.

Example 17: Stability Study of Crystalline Eltrombopag Monoethanolamine Salt Form D Crystalline stability of Form D was studied under accelerated ICH guideline conditions (T=40° C./75±5% RH).

ETP monoethanolamine salt Form D obtained in the Example 8 by AcOEt distillation (Table 4—Entry 1) was stored on a XRPD sample holder (10 mg) and exposed to ICH guideline accelerated stability conditions in the appropriate climate chamber (45±2° C.-75±5% RH). This sample was periodically analysed by XRPD in order to observe possible crystalline transformation or amorphization.

The crystalline Eltrombopag monoethanolamine salt Form D remains stable for at least 14 weeks and said period could also be much longer. (The analysis has been carried out for 14 weeks).

The results show that during that study period, the crystalline ETP monoethanolamine salt Form D has remained stable, indeed polymorphic transition, hydrate formation or amorphization was not observed.

Moreover, a sample of ETP monoethanolamine salt Form D stored on a XRPD silicon holder was exposed in a climatic chamber. It is worth noting that these stability conditions are harsher than standard stability conditions due to the high surface of exposition of the solid stored on the XRPD silicon holder. The samples were periodically analysed by XRPD to observe possible crystalline transformation.

Finally, said that Eltrombopag monoethanolamine salt Form D has a good stability, and therefore is well suitable for pharmaceutical purposes, it has the best solubility in water and the best non-hygroscopic behaviour. Said features provide advantages in pharmaceutical compositions comprising ETP monoethanolamine salt Form D.

The invention claimed is:

1. Crystalline Eltrombopag monoethanolamine salt Form D of formula (I):

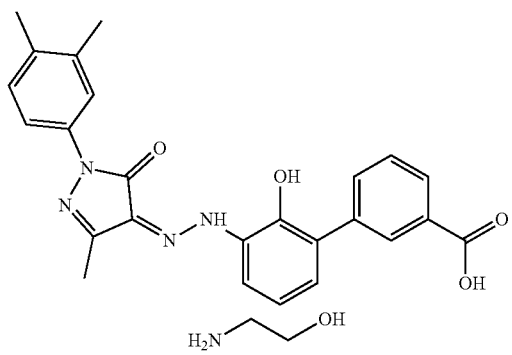

(I)

having one of the following characteristic peaks of X-ray powder diffraction pattern expressed in 2-Theta values (2θ) at: 7.8, 11.1 and 19.1, each peak±0.2.

2. The crystalline Eltrombopag monoethanolamine salt Form D according to claim 1, having two or three of the following characteristic peaks of X-ray powder diffraction pattern expressed in 2-Theta values (2θ) at: 7.8, 11.1 and 19.1, each peak±0.2.

3. The crystalline Eltrombopag monoethanolamine salt Form D according to claim 1, having characteristic peaks of X-ray powder diffraction pattern expressed in 2-Theta values (2θ) at: 7.8, 8.6, 11.1, 18.9 and 19.1, each peak±0.2.

4. The crystalline Eltrombopag monoethanolamine salt Form D according to claim 1, having DSC onset in the range of from 231° C. to 233° C. and/or DSC peak in the range of from 237° C. to 239° C.

5. A process for the preparation of the crystalline Eltrombopag monoethanolamine salt Form D of formula (I):

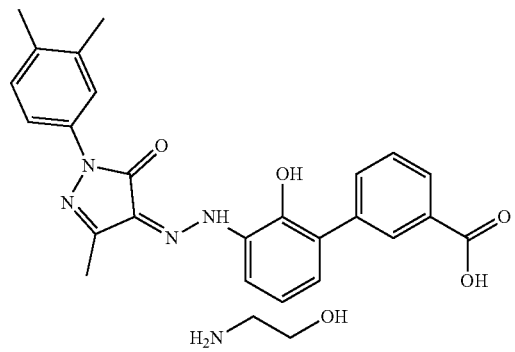

(I)

comprising:
a) salifying Eltrombopag in a solvent with ammonia to give a crystalline Eltrombopag ammonium salt Form C1 or crystalline Eltrombopag ammonium salt Form C2 or mixture thereof,
b) providing a suspension of the product of the step a) in a solvent and ethanolamine, and
c) distilling the mixture of the step b) to give crystalline Eltrombopag monoethanolamine salt Form D of formula (I):

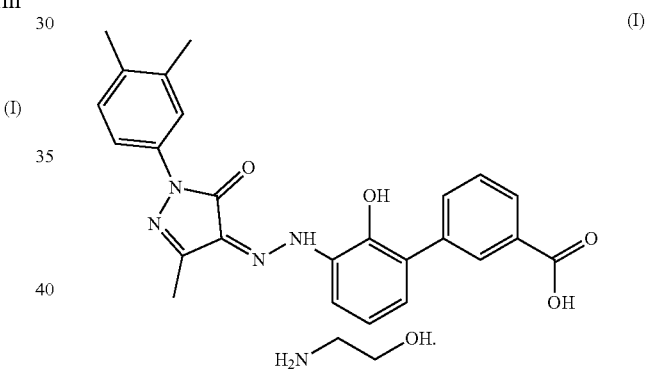

(I)

6. The process according to claim 5, wherein in step a) Eltrombopag is suspended in a solvent.

7. The process according to claim 5, wherein the salification of the step a) is carried out at temperature of from 20° C. to 50° C.

8. The process according to claim 5, wherein the salification of the step a) is carried out in a ketone, alcohol, nitril, ester, aromatic or ether solvent.

9. The process according to claim 5, wherein in step a) the crystalline Eltrombopag ammonium salt Form C1 has characteristic peaks of X-ray powder diffraction pattern expressed in 2-Theta values (2θ) at: 12.5 and 22.5, each peak±0.3, or the crystalline Eltrombopag ammonium salt Form C2 has characteristic peaks of X-ray powder diffraction pattern expressed in 2-Theta values (2θ) at: 14.6, 15.8 and 17.6, each peak±0.3 or the mixture thereof.

10. The process according to claim 5, wherein the solvent of step b) is ethyl acetate.

11. Crystalline Eltrombopag ammonium salt Form C1 having characteristic peaks of X-ray powder diffraction pattern expressed in 2-Theta values (2θ) at: 12.5 and 22.5, each peak±0.3.

12. The crystalline Eltrombopag ammonium salt Form C1 according to claim 11, having characteristic peaks of X-ray powder diffraction pattern expressed in 2-Theta values (2θ) at: 5.0, 10.4, 12.5, 22.5 and 24.4, each peak±0.3.

13. Crystalline Eltrombopag ammonium salt Form C2 having characteristic peaks of X-ray powder diffraction pattern expressed in 2-Theta values (2θ) at: 14.6, 15.8 and 17.6, each peak±0.3.

14. A pharmaceutical composition comprising a crystalline Eltrombopag monoethanolamine salt Form D according to claim 1, and one or more pharmaceutically acceptable excipients.

15. A method for the treatment of chronic immune thrombocytopenia comprising administering the Crystalline Eltrombopag monoethanolamine salt Form D of claim 1 to a patient in need thereof.

* * * * *